United States Patent [19]

Dvorak

[11] 4,041,611
[45] Aug. 16, 1977

[54] MEANS OF MEASURING A PUPPY'S TAIL FOR SURGICALLY DOCKING THE SAME

[76] Inventor: Vernon B. Dvorak, 7211 Hickory Grove Road, Cary, Ill. 60013

[21] Appl. No.: 605,250

[22] Filed: Aug. 18, 1975

[51] Int. Cl.² .......................... B43L 9/08; A61B 5/10
[52] U.S. Cl. ................................. 33/174 D; 33/192
[58] Field of Search .............. 33/192, 174 D, 137 R, 33/137 L; 128/305 R, 116

[56] References Cited

U.S. PATENT DOCUMENTS 1,303,756  5/1919  Ballou .............................. 33/137 R

FOREIGN PATENT DOCUMENTS 106,257  5/1917  United Kingdom .................. 33/192

Primary Examiner—Steven L. Stephan
Attorney, Agent, or Firm—Zarley, McKee, Thomte, Voorhees & Sease

[57] ABSTRACT

A puppy tail docking gauge comprising a lazy-tong device comprised of a plurality of tong elements pivotally secured together to form pivotally secured tong sections, with the tong sections pivotally secured together by hollow rivets and a guide bar secured to one end of the lazy-tong device. The method comprising straightening the puppy's tail over the lazy-tong device, adjusting the length of the lazy-tong device so that the tip of the tail extends to a point of pivotal connection between two adjacent tong sections, marking the tail at such point, and surgically docking the tail at said point.

1 Claim, 5 Drawing Figures

MEANS OF MEASURING A PUPPY'S TAIL FOR SURGICALLY DOCKING THE SAME

BACKGROUND OF THE INVENTION

Appearance standards for different breeds of dogs have been well established over the years. Selective breeding has replaced the natural selection of the wild state since domestication in an attempt by man to accentuate the characteristics desired of an individual breed. Man further determined genetic improvement was not sufficient in that utility and appearance could be enhanced by physical changes in body confirmation. Ear cropping and tail docking became two widely accepted practices to effect this change for certain breeds. The tails of puppies are normally docked within one week of age.

Standards for tail lengths for specific breeds of dogs requiring this confirmation change have been established. These standards vary from breed to breed. A few of the variations are as follows:

| BREED | LENGTH AT LESS THAN ONE WEEK OF AGE |
| --- | --- |
| Sporting dogs: | |
| Cocker | Leave 1/3 |
| German Short Haired Pointer | Leave 2/5[a] |
| Vizla | Leave 2/3[a] |
| Wire Haired Pointing Griffen | Leave 1/3[a] |
| Terrier breeds: | |
| Airedale Terrier | Leave 2/3–3/4[b] |
| Fox Terrier (smooth and wire) | Leave 2/3–3/4[b] |
| Australian Terrier | Leave 2/5[a] |
| Irish Terrier | Leave 3/4[a] |
| Sealyham | Leave 1/2–1/2 |
| Toy Breeds: | |
| Toy Poodle | Leave 1/2–2/3 |
| Yorkshire | Leave 1/3–1/2 |
| Minature Poodle | Leave 1/2–2/3 (about 1 1/8 in.) |
| Standard Poodle | Leave 1/2–2/3 (about 1 1/2 in.) |

[a] Taken from official breed standards.
[b] The tip of the tail should be approximately level with the head in show position.

The veterinarian performing this surgery by approximating and not actually measuring the fraction distances will over a period of time become very proficient at determining the proper lengths to be removed but this is still an approximation with a margin for error. On the other hand, the surgeon measuring the lengths will periodically encounter difficult and time-consuming problems.

1. Each puppy in the litter may require measuring if the individuals vary in size.
2. The computation of total tail length in inches or metric distance and its fractional removal is tedious and difficult to determine. Example:
   2/5 of 3⅛ inches
   ⅜ of 2½ inches The device and method of this invention will quickly and easily identify fractional tail lengths to be removed without time-consuming measurements or nonmeasured approximations. The invention functions on the principle of maintaining equidistant marking points regardless of the length measured merely extension or contraction of the instrument. Hence fifths, fourths, thirds and halves are quickly ascertained. Its application by the veterinarian will enable him to:

1. Identify surgical tail amputation sites of the various breeds of dogs as determined by standards set for a specific breed.
2. Accurately determine this proportion regardless of the size of the individual animal or the variance of tail lengths in a litter.

Breeders may find the instrument helpful in premarking certain litters for specific desired tail lengths prior to the veterinary hospital visit.

BRIEF DESCRIPTION OF THE DRAWINGS

This invention consists in the construction, arrangements and combination of the various parts of the device, whereby the objects contemplated are attained as hereinafter more fully set forth, specifically pointed out in the claims, and illustrated in the accompanying drawings in which:

DESCRIPTION OF THE PREFERRED EMBODIMENT

Figure 1:
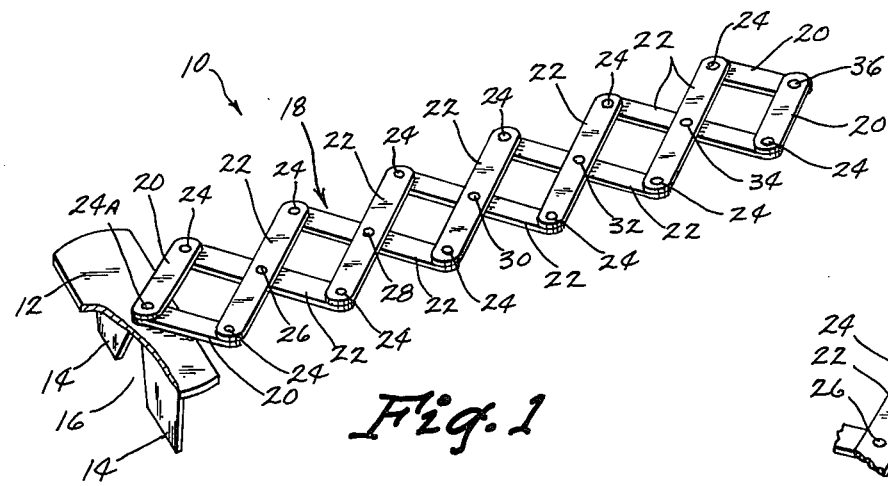
FIG. 1 is a perspective view of the tail docking gauge.
Figure 2:
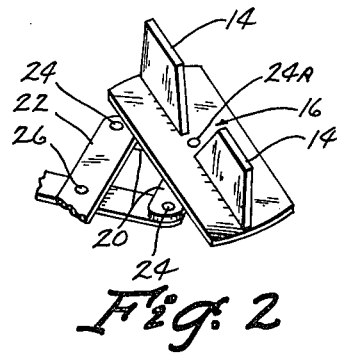
FIG. 2 is a partial perspective view of the side of the guide bar opposite to that shown in FIG. 1.

In the drawings, the numeral 10 refers generally to the gauge which is comprised of a guide bar 12 having a flange 14 extending vertically therefrom with a V-notch 16 therein. The notch 16 is centered on the flange 14.

A lazy-tong unit 18 is comprised of a plurality of bars or tong elements 20 and 22. The outer ends of the bars 20 and 22 are pivotally secured together by pins or the like 24. The bars 22 have a length substantially twice the length of bars 20. A pin 24A pivotally secures two of the bars 20 to the guide bar 12 at a point directly centered at the bottom of notch 16.

As shown in FIG. 1, hollow rivets 26, 28, 30, 32, 34 and 36 pivotally secure together the inner midpoints of the bars 22 and the outer extreme ends of the two bars 20 which are located at the end of the gauge opposite to the guide bar 12. These rivets divide the lazy-tong unit 18 into six tong sections, the significance of which will be discussed more fully hereafter.

Figure 3:
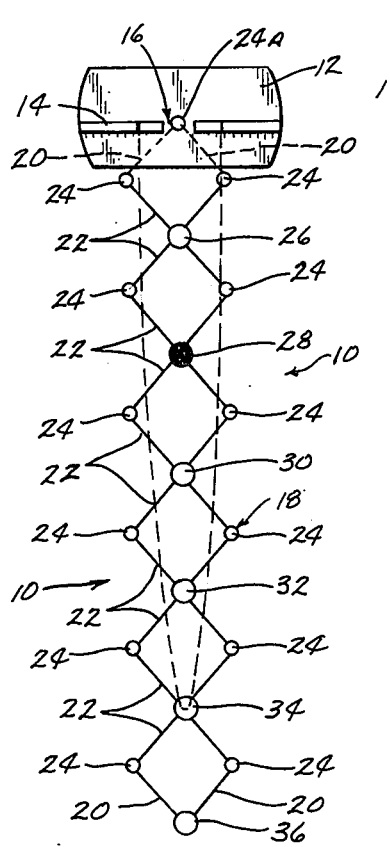
FIG. 3 is a schematic view of the gauge as it would be used to measure two-fifths of a large tail of a puppy.

In operation, the tail of the puppy is positioned in the V-slot 16 with the guide bar 12 in engagement with the pelvic bones of the puppy. The tail is then straightened over the lazytong unit 18. FIG. 3 illustrates the manner in which the lazytong unit is adjusted so that two-fifths of the tail can be removed. The unit 18 is elongated so that the tip of the tail extends to the fifth tong section at a point over rivet 34. The five tong sections between pin 24A and hollow rivet 34 thus divide the tail into five increments. The moistened tip of a colored pencil or the tip of a felt pin is then inserted downwardly through rivet 28 so that a visible mark is placed on the tail. The hollow rivet 28 defines two of the five aforementioned sections, and thus the mark placed on the tail through this rivet thus defines two-fifths of the length of the actual tail. It should be appreciated that two-fifths of the length of the tail has thus been determined without taking any actual measurement of the tail.

Figure 4:
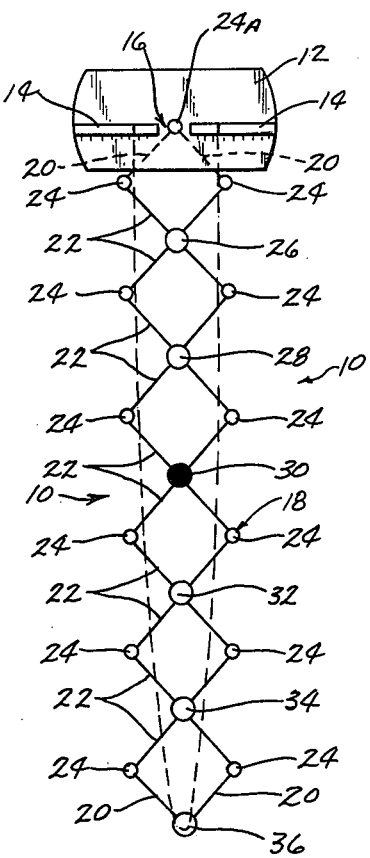
FIG. 4 is a schematic view of the gauge as it would be used to measure one-half of a large tail of a puppy.

Similarly, FIG. 4 shows how one-half the length of a relatively large tail would be marked and docked. The lazytong unit is extended so that the tip of the tail coincides with the hollow rivet 36 at the end of the unit. The marking is then effected through the center hollow rivet 30. Thus, the tail has been "divided" into six equal sections, and the mark has been made at a point three sections away from the reference pin 24A.

Figure 5:
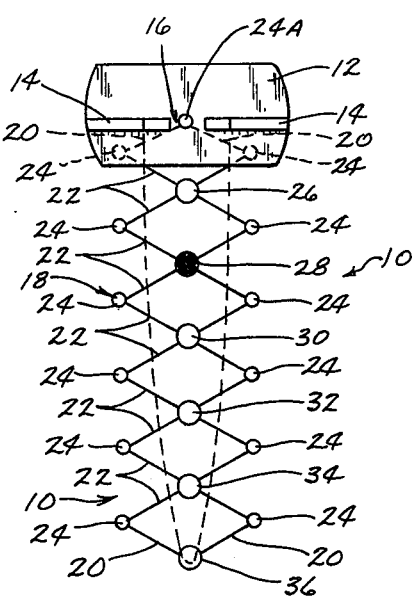
FIG. 5 is a schematic view of the gauge as it would be used to measure one-third of the tail of a small puppy.

The schematic drawing of FIG. 5 is similar to that of FIG. 4 but depicts the manner in which two-thirds of a small tail can be removed. This is accomplished by placing the tip of the tail adjacent the last hollow rivet 36, and then effecting the marking through the second hollow rivet 28.

After the tails have been marked as described above, the tail is removed at the point of the mark. A V-flap incision will require cutting slightly posterior to the marked center.

Thus, from the foregoing, it is seen that this invention will accomplish at least its stated objectives.

What is claimed is:

1. A puppy tail docking gauge comprising:
   a lazy-tong means comprised of a plurality of tong elements pivotally secured together to form pivotally secured tong sections; said lazy-tong means including an end tong section comprised of two tong elements, means pivotally connecting said two tong elements to define an end pivot point,
   a flat guide bar means secured to said end pivot point and dwelling in substantially the same plane as said lazy-tong means, said guide bar means adapted to engage the pelvic bone of the puppy whose tail is to be docked,
   a flange means on said flat guide bar means extending transversely with respect thereto and generally at right angles with respect to said lazy tong means, said flange means dwelling in the same plane as said end pivot point,
   said flange means having a centrally disposed opening formed therein for receiving the tail of the puppy as the tail is extended along said lazy-tong means.

* * * * *